United States Patent [19]

Canfield et al.

[11] Patent Number: 4,792,528
[45] Date of Patent: * Dec. 20, 1988

[54] METHODS FOR OBTAINING MONOCLONAL ANTIBODIES USEFUL IN ENHANCED SENSITIVITY IMMUNOASSAYS

[75] Inventors: Robert E. Canfield; Paul H. Ehrlich, both of New York, N.Y.; William R. Moyle, Piscataway, N.J.

[73] Assignee: The Trustees of Columbia University in the City of New York, New York, N.Y.

[ * ] Notice: The portion of the term of this patent subsequent to Apr. 30, 2002 has been disclaimed.

[21] Appl. No.: 16,213

[22] Filed: Feb. 19, 1987

Related U.S. Application Data

[63] Continuation of Ser. No. 728,853, Apr. 30, 1985, which is a continuation of Ser. No. 380,959, May 21, 1982, Pat. No. 4,514,505.

[51] Int. Cl.[4] ............... G01N 33/537; G01N 33/561; G01N 33/577
[52] U.S. Cl. ...................... 436/515; 435/7; 435/68; 436/510; 436/516; 436/518; 436/536; 436/548; 935/108; 935/110; 530/387
[58] Field of Search ............ 435/7, 68; 436/548, 436/510, 514–515, 518, 536; 935/106–108, 110; 530/387

[56] References Cited

U.S. PATENT DOCUMENTS

| | | | |
|---|---|---|---|
| 4,088,746 | 5/1978 | Blakemore | 424/1 |
| 4,098,876 | 7/1978 | Piasio | 424/1 |
| 4,108,976 | 8/1978 | Reese | 424/1 |
| 4,244,940 | 1/1981 | Jeong | 424/1 |
| 4,248,965 | 2/1981 | Mochida | 435/7 |
| 4,376,110 | 3/1983 | David | 436/513 |
| 4,471,058 | 9/1984 | Smith | 436/518 |
| 4,474,892 | 10/1984 | Murad | 436/513 |
| 4,496,658 | 1/1985 | Kondo | 436/510 |
| 4,514,505 | 4/1985 | Canfield | 436/500 |
| 4,520,226 | 5/1985 | Neville, Jr. | 424/85 |
| 4,522,922 | 6/1985 | Carro | 436/500 |

FOREIGN PATENT DOCUMENTS

| | | | |
|---|---|---|---|
| 0044219 | 1/1982 | European Pat. Off. | 435/7 |
| 2078953 | 1/1982 | United Kingdom | 436/540 |

OTHER PUBLICATIONS

Koprowski, H. et al., Proc. Natl. Acad. Sci., U.S.A., vol. 75(7), pp. 3405–3409 (1978) cited in Biocis Abstract No. 67016885.
Steensgaard, J. et al., Immunology, vol. 32, pp. 445–456 (1977).
Webster, R. G. et al., Virology, vol. 104(1), pp. 139–148 (1980) cited in Biosis Abstract No. 70061846.
Steensgaard, J. et al., Molecular Immunology, vol. 17, pp. 1315–1318 (10–1980).
Jefferis, R. et al., J. Immunol. Methods, vol. 39(4), pp. 355–362 (1980).
Gupta, S. K. et al., Canadian J. Exper. Biol., vol. 18, pp. 1361–1365 (12–1980).
Uotilla, M. et al., J. Immunol. Methods, vol. 42, pp. 11–15 (1981).
Brown, J. P. et al., Clin. Chem., vol. 27(9), pp. 1592–1596 (1981).
Tosi, R. et al., European J. Immunology, vol. 11, pp. 721–726 (9–1981).
Aikawa, M. et al., J. Protozool., vol. 28(3), pp. 383–388 (1981) cited in Biosis Abstract No. 73068894.

(List continued on next page.)

Primary Examiner—Margaret M. Moskowitz
Attorney, Agent, or Firm—John P. White

[57] ABSTRACT

Mixtures of monoclonal antibodies which contain effective assaying amounts of each of at least two monoclonal antibodies that bind to different antigenic sites on the antigen and are capable under appropriate conditions of binding simultaneously to an antigen are useful in enhanced sensitivity assays for the antigen. By utilizing such mixtures in diagnostic assays for important antigens such as the polypeptide human chorionic gonadotropin enhanced sensitivity can be achieved as compared with assays employing individual monoclonal antibodies.

2 Claims, 4 Drawing Sheets

OTHER PUBLICATIONS

Khazaeli, M. B. et al., Endocrinology, vol. 109(4), pp. 1290–1292 (1981).

Lemke, H. et al., Research Monographs in Immunology, vol. 3, pp. 102–109 (1981).

Schonherr, O. T. et al., Develop. Biol. Standards, vol. 50, pp. 235–242 (1982).

Bosch, A. M. G. et al., Protides Biol. Fluids, vol. 29, pp. 837–842 (1982) cited in Chemical Abstract 96: 215701x.

Sprent, J. et al., J. Exp. Med., vol. 154(1), pp. 188–192 (1981) cited in Biosis Abstract 73032175.

Hurrell, J. G. R. et al., J. Immunological Methods, vol. 45, pp. 249–254 (1981).

Shimuzu, S. Y. et al., Clinical Chemistry, vol. 28(3), pp. 546–547 (1982).

Ehrlich, P. H. et al., Science, vol. 221, pp. 279–281 (7-1983).

Moyle, W. R. et al., Proc. Natl. Acad. Sci., U.S.A., vol. 79, pp. 2245–2249 (4-1982).

Ehrlich, P. H. et al., J. of Immunology, vol. 128(6), pp. 2709–2713 (6-1982).

Wada, H. G. et al., Clin. Chem., vol. 28(9), pp. 1862–1866 (9-1982).

Buchegger, F. et al., Immunology Letters, vol. 5, pp. 85–91 (1982).

Imai, M. et al., J. of Immunology, vol. 128(1), pp. 69–72 (1-1982).

Holmes, N. J. et al., J. Biol. Chem., vol. 288(1), pp. 1580–1582 (2-1983).

Moyle, W. R. et al., Molecular Immunology, vol. 20, pp. 439–452 (4-1983).

Howard, J. C. et al., Immunol. Rev., vol. 47, pp. 139–174 (1977). See pp. 147, 148 160–168.

Berger, P. et al., Immunobiology, vol. 160(1), p. 5 (1987).

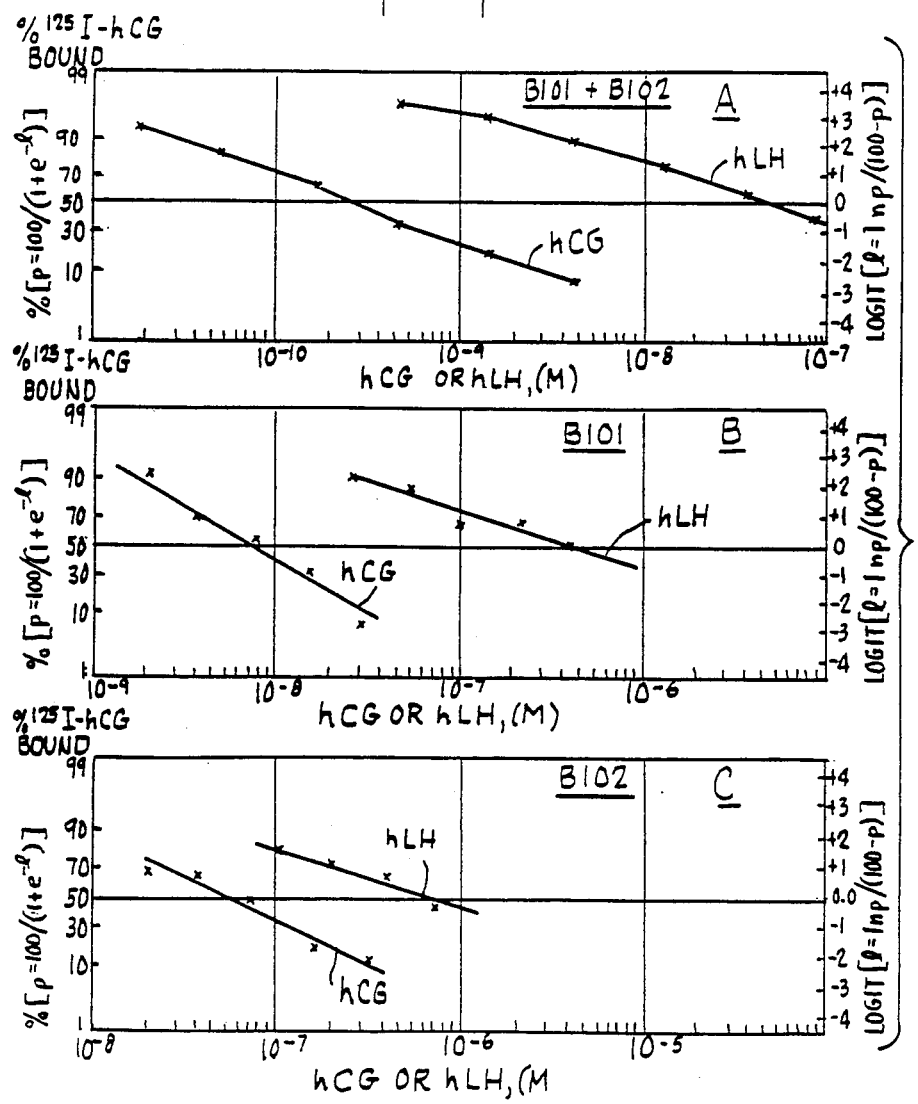

METHODS FOR OBTAINING MONOCLONAL ANTIBODIES USEFUL IN ENHANCED SENSITIVITY IMMUNOASSAYS

The invention described herein was made in the course of work under grants numbered HD-13496, HD-15454 and CA-26636 from the National Institutes of Health, United States Department of Health and Human Services.

This is a continuation of U.S. Ser. No. 728,853, filed Apr. 30, 1985, which was a continuation of U.S. Ser. No. 380,959, filed May 21, 1982, now U.S. Pat. No. 4,514,505, issued Apr. 30, 1985.

BACKGROUND OF THE INVENTION

Development of the hybridoma technology [Kohler, G., and C. Milstein, (1975) Nature 256: 495 and; Goding, J. W., (1980) Immunological Methods 39: 285] has provided immunoglobulin reagents which bind to only one antigenic site. Although these reagents have found widespread use as biochemical and immunological tools, their usefulness in radioimmunoassay has frequently been limited by their lower affinity for antigen compared with that of serum antibodies [Goding, J. W., (1980) Immunological Methods 39: 285]. In principle, the affinity of monoclonal antibodies could be enhanced by more stringent hybridoma selection procedures. The production of monoclonal antibodies has also enabled investigators to dissect the humoral immune response into its pure components [Staines, N. A. and A. M. Lew (1980), Immunology 40: 287]. This will eventually result in a more comprehensive understanding of the role of the individual antibody, especially with regard to the possibility that an antiserum may have different characteristics than the sum of its individual antibodies.

During the course of a systematic assessment of the immunochemistry of human chorionic gonadotropin (hCG), including the relative orientation of different epitopes of this molecule and the effect of several monoclonal antibodies on the hormone-receptor interaction, it has been observed that the apparent affinity of mixtures of certain monoclonal antibodies is enhanced relative to the affinity of the individual antibodies.

SUMMARY OF THE INVENTION

A mixture of monoclonal antibodies which includes an effective assaying amount of each of at least two monoclonal antibodies that bind to different antigenic sites on an antigen and are capable of doing so under appropriate conditions is useful in an enhanced sensitivity assay for the antigen.

Such mixtures are particularly useful in assays for antigens having multiple epitopes, e.g. polypeptides such as human chorionic gonadotropin, follicle stimulating hormone, thyroid stimulating hormone or luteinizing hormone where the different antigenic sites on the antigen are different amino acid sequences contained therein. By employing such mixtures in assays for antigens of clinical interest one can obtain enhanced sensitivity as compared with the sensitivity obtained with the individual monoclonal antibodies.

BRIEF DESCRIPTION OF THE DRAWINGS

FIG. 7: Logit inhibition curves of A: a mixture of B01 and B102, B: antibody B101 and C: antibody B102 with hCG and with human luteinizing hormone (a hormone with a very similar structure).

DETAILED DESCRIPTION OF THE INVENTION

Figure 1:
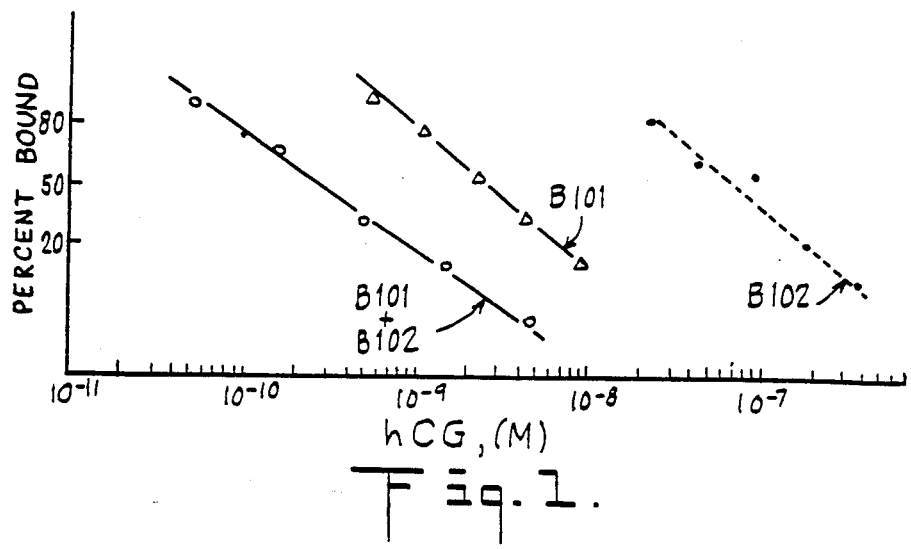
FIG. 1: Radioimmunoassay for human chorionic gonadotropin (hCG) by double antibody liquid phase assay. The amount of labeled hCG bound in the absence of unlabeled inhibitor was approximately the same for each antibody or antibody mixture. This was achieved by appropriate dilution of each antibody solution or mixture. Rabbit anti-mouse IgG was the second antibody. The ED$_{50}$ plus/minus the standard deviation was calculated for each antibody or mixture. The ED$_{50}$ for the mixture of B101 and B102 is $2.44 \pm 0.74 \times 10^{-10}$M, antibody B101 is $2.88 \pm 0.74 \times 10^{-9}$M, and antibody B102 is $1.058 \pm 0.995 \times 10^{-7}$M.

It has been observed that mixing monoclonal antibodies directed against various epitopes of human chorionic gonadotropin can increase the sensitivity of antigen binding assays. Depending on the antibody pair chosen, the affinity of the mixture can be as much as 10-fold higher than that of the monoclonal antibodies assayed separately. This increased affinity can be detected in both a solid phase assay and a liquid phase double antibody radioimmunoassay. The mechanism for the increase in affinity depends on the formation of a multicomponent complex. Mixing two antibodies which cannot bind simultaneously does not result in enhanced affinity, but combining pairs which can bind at the same time under appropriate conditions results in higher sensitivity in an antigen binding assay. If one of the antibodies of a pair which results in enhanced affinity upon mixing is replaced by its F(ab) fragment, the enhancement is no longer detectable, indicating that it is unlikely that the enhancement is due to an allosteric effect. While the F(ab')$_2$ fragment shows some enhancement when mixed with another antibody, it is not as effective as the intact antibody.

Based upon these discoveries and observations, the present invention provides mixtures of monoclonal antibodies useful in an enhanced sensitivity assay for an antigen. The antibodies useful in the practices of the inventions are also characterized by the fact that they are capable of binding to the antigen both under normal nondenaturing conditions and under conditions described hereinafter where antibodies otherwise capable of binding to the antigen are unable to do so.

The invention described herein may in principle involve more than two monoclonal antibodies. Mixtures containing three, four or more antibodies each of which binds to a different antigenic site on the antigen may be particularly useful in assays for large molecules such as polypeptides having numerous subunits. However, for illustrative purposes the invention will be described by reference to mixtures which contain two such antibodies.

Although various types of antigens could be detected in assays employing mixtures of suitable monoclonal antibodies, the invention is particularly suited for detection of polypeptide antigens where the different antigenic sites are different and distinct amino acid sequences contained within the polypeptide. Examples of antigens of this type are the sequence related hormones human chorionic gonadotropin (hCG), follicle stimulating hormone (FSH), thyroid stimulating hormone (TSH) and luteinizing hormone (LH).

To be effective in assay, each monoclonal antibody of the assay mixture should be present in an amount sufficient to permit significant binding to the antigen, that is, above about 10 percent of the antigen to be simultaneously bound to the antibodies. Preferably the amount of antigen bound should be higher, for example an amount in the range from about 20 to about 80 percent or higher.

In order to obtain such amounts of bound antigen, the precise amount of each antibody may vary widely depending upon its affinity for the antigen so that lesser amounts of antibodies having higher affinities are required than of antibodies having lower affinities.

The amounts of each of the monoclonal antibodies relative to one another will also vary over a wide range. For a two antibody mixture, the amount may vary from about $10^6$:1 to 1:$10^6$. However, based upon the binding constants most likely to characterize the monoclonal antibodies of interest the range might preferably be from about $10^2$:1 to 1:$10^2$. In general, the preferred amount of each antibody relative to the amount of other antibodies will be substantially the same as the ratio of the binding constants of the antibodies to the antigen. Thus, if the binding constants of monoclonal antibodies A and B are $10^{-9}$ and $10^{-7}$, respectively, the relative amounts of A and B will be about $10^{-9}/10^{-7} = 10^{-2}$, that is, 1 molecule of A for each 100 molecules of B.

In the case of polypeptide antigens which contain subunits such as the $\alpha$ and $\beta$ subunits of human chorionic gonadotropin, mixtures of monoclonal antibodies in which each of the antibodies binds to an antigenic site on a different subunit are more likely to provide enhanced sensitivity in assays employing them, possibly because they are more likely to be capable of simultaneously binding to the antigen under appropriate conditions.

The mixtures may be used in assays in different forms. Thus, they may be used in solid form absorbed onto a solid matrix or in liquid form dissolved in a suitable buffered solution.

The mixtures can be employed in conventional immunoassays, including radioimmunoassays, to determine qualitatively and quantitatively the presence of antigens in samples of interest. In such methods the samples are contacted with the mixture under suitable conditions permitting formation of a detectable complex between the mixture and the antigen. One specific application would involve detection of human chorionic gonadotropic as a test for pregnancy.

To assist in an understanding of the invention the results of a series of experiments follow. Of course, these experiments are intended merely to illustrate the invention and should not in any way be construed as limiting its scope as defined by the claims which follow thereafter.

EXPERIMENTAL DETAILS

Materials and Methods

Production of Monoclonal Antibodies:

Balb/c mice were immunized monthly with an intraperitoneal injection of hCG subunits in complete Freund's adjuvant for several months according to the method of Wands and Zurawski [Wands, J. R., and V. R. Zurawski, (1981) Gastroenterology 80: 225]. Three days before the spleen was excised, additional antigen was injected (50 $\mu$g, I.V., in saline).

The spleen cells were fused with P3-NS1/1-Ag4-1 myeloma cells and hybridoma cells were isolated using published procedures [Wands, J. R., and V. R. Zurawski, (1981) Gastroenterology 80: 225; Marshak-Rothstein, A., et al., (1979) J. Immunol. 122: 2491]. Antibodies used for subsequent studies were isolated from hybridoma cell lines which were cloned twice by limiting dilution on Balb/c 3T3 monolayers. The antibodies are named with a letter and three numbers. The letter B indicates the antibody is specific for the $\beta$ subunit of hCG and A indicates the antibody binds the $\alpha$ subunit.

Cell supernatant, partially purified, or purified antibody, or both were used. To obtain partially purified antibody the hybridoma cells were grown in serum-free medium containing 2 mg/ml bovine serum albumin and the supernatant dialyzed against 0.05M ammonium bicarbonate. After lyophilization, the powder was reconstituted in the desired volume of 0.3M potassium phosphate buffer, pH 7.5. To obtain purified antibody the same protocol was followed (except the medium contained 0.1 mg/ml bovine serum albumin) and the albumin removed with a DEAE Affi-Gel Blue column (Bio-Rad Laboratories).

Double Antibody Radioimmunoassay:

50 $\mu$l $^{125}$I-hCG and 50 $\mu$l of unlabeled hCG (both in 1 percent horse serum, 99 percent phosphate buffered saline) were mixed with 100 $\mu$l 0.3M potassium phosphate (pH 7.5). Subsequently, 100 $\mu$l antibody (diluted in 1 percent horse serum) were added, the tubes incubated one hour at 37° C. followed by 18 hours at 5° C., and the complex precipitated by adding 10 $\mu$l of 50 percent normal mouse serum (in phosphate buffered saline) and an appropriate amount of rabbit anti-mouse IgG or goat anti-mouse F(ab')$_2$. Once precipitation was complete (i.e. 10 minutes at 37° C. and then 1 hour at room temperature), the precipitate was sedimented and counted.

Solid Phase Radioimmunoassay:

To coat plastic microtiter wells with antibody, 50 $\mu$l purified antibody was incubated for 18 hours at 5° C. in a Cooke microtiter plate ("U" wells) and excess non-bound antibody removed by washing the wells three times with distilled water. To saturate all the plastic sites which would bind proteins, the plates were treated with 10 percent γ-G free horse serum (90 percent phosphate buffered saline) for 2 hours and the excess removed with distilled water. HCG binding was quantified by adding 50 μl $^{125}$I-hCG in 1 percent horse serum containing varying amounts of hCG. After an incubation of 18 hours at 5° C., excess radioactivity was removed, the plates washed with distilled water and the wells counted.

Sandwich Assay:

50 μl containing at least 30 μg/ml of monoclonal antibody were added to the 96-well microtiter plates to permit the antibody to adsorb to the surface of the plastic. After 4 hours at 37° C. the solution was removed and the plates immersed in 150 mM NaCl solution containing 1 mg/ml bovine serum albumin (BSA-saline) to fill remaining non-specific adsorption sites on the plastic surface. To saturate the antibodies with hCG, the hormone (1 μg in 50 μl BSA-saline) was added for 2 hours to each microtiter well. Under these conditions most of the hCG which became insolubilized was bound to antibody adsorbed to the plastic. Excess hCG was removed by washing the plate in BSA-saline solution. After addition of radiolabeled antibody (50,000–100,000 cpm in BSA-saline solution for 2 hours at room temperature), the non-bound label was removed by washing the plate in BSA-saline, the microtiter plates cut apart with scissors, and the radioactivity adsorbed to each well was measured.

Other Materials and Methods:

Digestion of antibody B102 was performed by methods previously described [Edelman, G. M., and J. J. Marchalonis, (1967) Methods in Immunology and Immunochemistry, Vol. I, pp. 405, Academic Press, New York]. Sodium dodecyl sulfate (NaDodSO$_4$) polyacrylamide gel electrophoresis [Weber, K., and M. Osborn, (1969) J. Biol. Chem. 244: 4406] of the digestion products indicated that essentially no complete heavy chain remained. The F(ab')$_2$ fragment of antibody B101 was prepared by pepsin digestion [Gorini, G., et al., (1969) J. Immunol. 103: 1132], except that the amount of pepsin was 2½ percent by weight of the amount of antibody. Antibody which remained undigested was removed by incubation with Protein A-Sepharose (Pharmacia Fine Chemicals) at pH 8.1 and centrifugation of the Protein A-Sepharose-antibody complex. Conditions were similar to those employed by Ey, et al. [Ey, P. L., et al., (1978) Immunochemistry 15: 429] except that a batch process instead of column chromatography was employed. NaDodSO$_4$ polyacrylamide gel electrophoresis in the absence of reducing agents revealed only one major band at a molecular weight of 105,000. The concentration of hCG was determined by the optical density at 280 nm and amino acid analysis. Chloramine-T was used to iodinate hCG according to the procedure described by Greenwood, et al. [Greenwood, F., et al., (1963) Biochem. J. 89: 114].

Results

Figure 2:
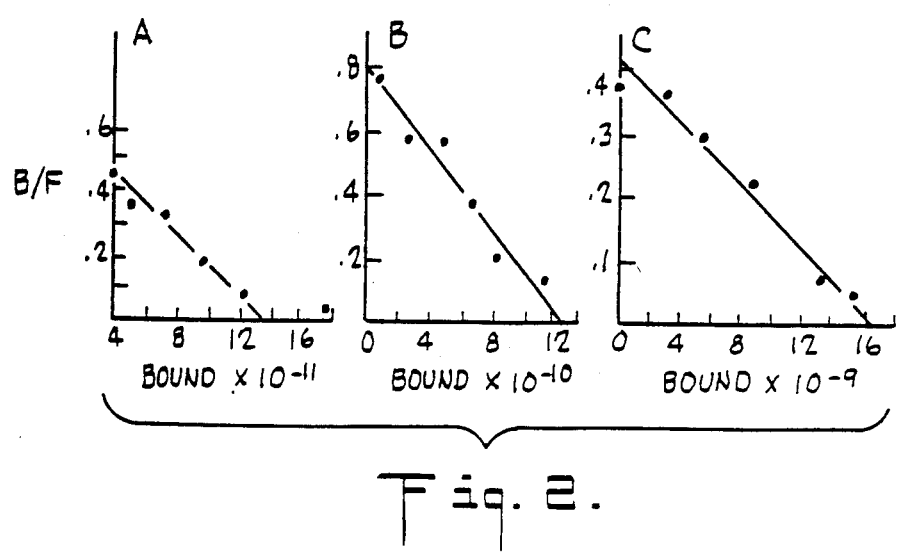
FIG. 2: Scatchard analysis of the binding to hCG of A, a mixture of antibodies B101 and B102; B, antibody B101 and C, antibody B102. Slopes of the lines (therefore, the equilibrium binding constants) are A: $5.4 \times 10^9$; B: $5.1 \times 10^8$; and C: $1.9 \times 10^7$.
Figure 3:
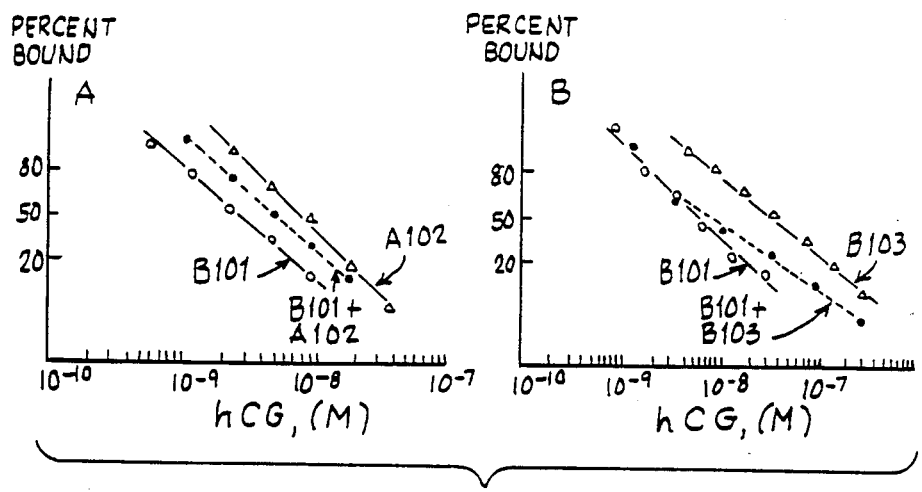
FIG. 3A: Radioimmunoassay for hCG by double antibody liquid phase assay. The procedure was the same as for FIG. 1. The ED$_{50}$ for antibody A102 is $8.52 \pm 2.94 \times 10^{-9}$M, antibody B101 is $2.88 \pm 0.74 \times 10^{-9}$M, and mixture of antibodies B101 and A102 is $4.66 \pm 1.99 \times 10^{-9}$M.
FIG. 3B: Radioimmunoassay for hCG by double antibody liquid phase assay with antibodies B101, B103, and a mixture of B101 and B103. The procedure was the same as in FIG. 1.

Radioimmunoassays:

The ability of hCG to inhibit the binding of radioiodinated hCG to monoclonal antibodies B101, B102, and a mixture of B101 and B102 was compared (FIG. 1). HCG was 20-fold more active in inhibiting binding of radiolabel when the mixture was employed. Scatchard analysis of the data showed a similar increase in affinity of the mixture over B101 alone and a much larger increase over B102 alone (FIG. 2). The greater affinity enabled us to dilute a 1:1 mixture of the two antibodies 9-fold and achieve the same amount of tracer binding as the separate antibodies. These results were highly reproducible, as shown in Table I. While the data are not presented here, the ability of two antibodies to show this cooperative effect is not limited to pairs of antibodies which bind the same subunit since A102 and B102 also have this cooperative interaction. Other combinations of antibodies did not produce the same result. Thus, a similar cooperative effect between B101 and A102 (FIG. 3A) or between B101 and B103 (FIG. 3B) was not observed.

TABLE I

Statistical Analysis of the Affinity of Antibodies B101 and B102 Compared with a Mixture of Antibodies B101 plus B102

| Experiment | Antibody or Mixture | Keq*(L/nMole) | Enhancement Factor** | P |
|---|---|---|---|---|
| 1 | B101 | 0.51 ± 0.02 | 10.6 | <.01 |
|  | B102 | 0.019 ± 0.002 |  |  |
|  | B101 + B102 | 5.4 ± 0.5 |  |  |
| 2 | B101 | 0.41 ± 0.09 | 7.3 | <.01 |
|  | B102 | 0.018 ± 0.002 |  |  |
|  | B101 + B102 | 3.0 ± 0.2 |  |  |
| 3 | B101 | 0.88 ± 0.08 | 5.7 | <.01 |
|  | B101 + B102 | 5.0 ± 0.07 |  |  |
| 4 | B101 | 0.81 ± 0.11 | 6.0 | <.01 |
|  | B101 + B102 | 5.5 ± 1.2 |  |  |

*Determined using Scatchard plots [Scatchard, G., (1949) Ann. N.Y. Acad. Sci. 51:660.]
**Keq for a mixture of B101 and B102 divided by Keq for B101. For the purposes of calculating the enhancement, the affinity of the mixture is compared to the affinity of the antibody with the higher affinity.

Figure 4:
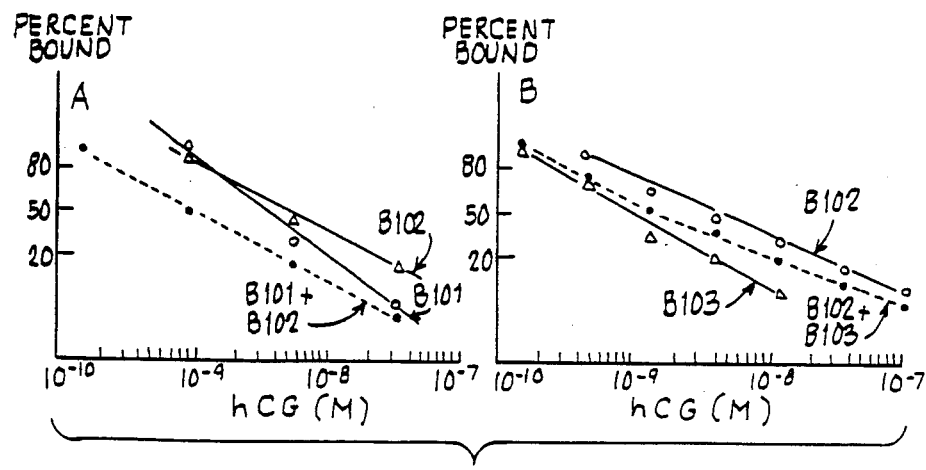
FIG. 4: Radioimmunoassay for hCG by solid phase assay. A: Antibodies B101, B102 and a mixture of B101 and B102. B: Antibodies B102, B103 and a mixtuure of B102 and B103.

Mixtures of B101 and A102 (or B101 and B103) gave inhibition curves intermediate between those antibodies. Similar results are apparent with a solid phase radioimmunoassay (FIG. 4). A mixture of B101 and B102 was observed to have a higher affinity of hCG than either of the antibodies separately, although the difference between the mixture and antibody B101 was only about 4-fold. The combination of antibody B102 and B103 did not result in an increase in affinity.

Sandwich Assays:

In order to obtain data bearing on the mechanism of the affinity change, the ability of the antibodies to bind the different sites on hCG was measured using sandwich assays (Table II). If unlabeled and radiolabeled antibody bind to the same site, the unlabeled antibody will inhibit binding of the radiolabel. Conversely, if both bind to different sites, a large amount of radiolabel will be bound to the plastic. Labeled and unlabeled B101 cannot bind the antigen at the same time; therefore, little radiolabel was observed bound to the plastic. Similar results were observed using labeled and unlabeled B102. Antibodies B102 and B103 bound to hCG at a site remote from that for B101 since both allowed binding of B101 to the plastic. Further, labeled B102 bound to hCG attached to unlabeled B101. In contrast, antibody A102 prevented binding of radioactive B101 indicating that A102 and B101 cannot bind simultaneously to hCG. Similarly, it was found that antibodies B102 and B103 cannot bind simultaneously. Thus, it appeared that simultaneous binding of the antibodies on two different hCG sites was necessary but not sufficient for cooperative interactions.

Figure 5:
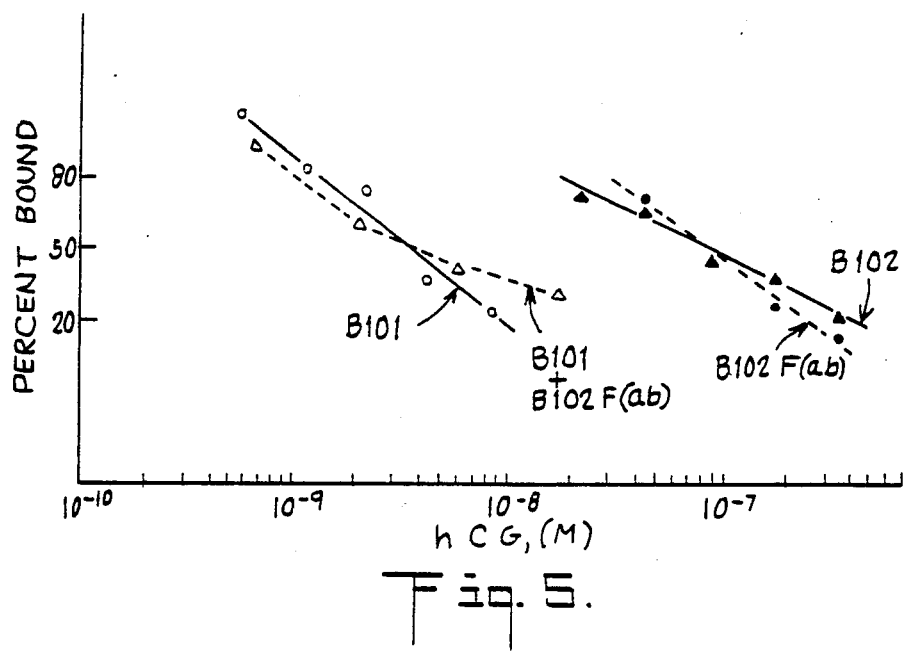
FIG. 5: Radioimmunoassay for hCG by double antibody liquid phase assay with papain digested B102. The procedure was the same as for FIG. 1 except that the second antibody used for precipitation of the antibody-antigen complex was goat anti-mouse F(ab')$_2$. The increase in affinity of the mixture was not affected by this change of second antibody (results not shown).
Figure 6:
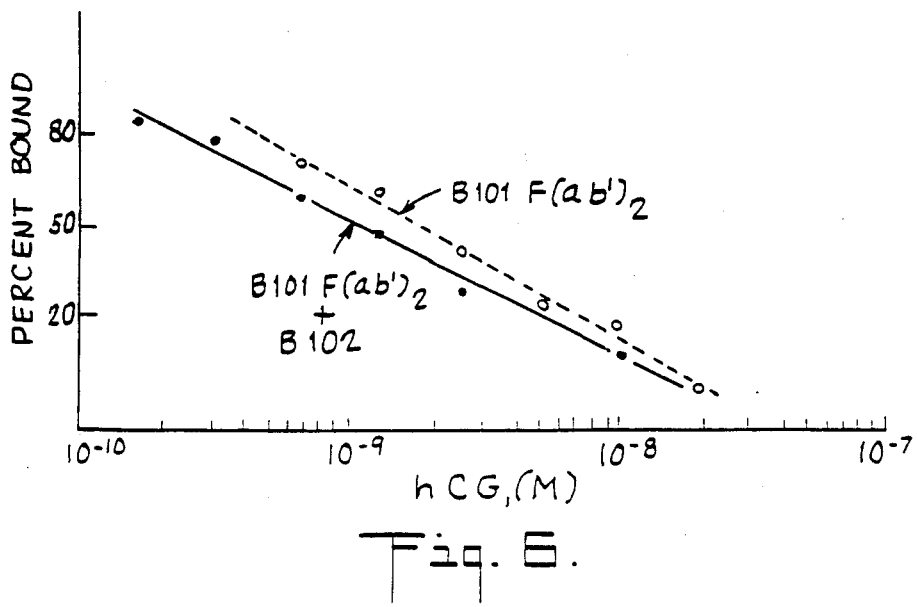
FIG. 6: Radioimmunoassay for hCG by double antibody liquid phase assay with B101-F(ab')$_2$. The procedure was the same as for FIG. 5.

Effect of Antibody Fragments:

To study the influence of the structure of the antibodies on cooperativity, fragments of the monoclonal antibodies were prepared. The capability of antibody B102 to enhance the affinity of B101 was eliminated when antibody B102 was digested with papain (FIG. 5) although papain digestion of B102 had no detectable effect on the affinity of this antibody for hCG. This indicated that either the F(c) region or the bivalency of the antibody was necessary for enhanced affinity. The bivalent F(ab')$_2$ results in some enhancement of binding affinity but it is not as effective as the intact antibody (FIG. 6 and Table III).

TABLE II

Sandwich Assays Using Pairs of Monoclonal Antibodies

| Labelled Antibody | Unlabeled Antibody | | | |
|---|---|---|---|---|
| | B101 | B102 | B103 | A102 |
| B101 | 17 | 9438* | 11128* | 415 |
| B102 | 5136* | −202 | 144 | 5453* |

Values are cpm (means of triplicate determinations) of antibody specifically bound to hCG-unlabelled antibody complexes adsorbed to the surface of the plastic microtiter plates. Radioactivity bound nonspecificaly (i.e. that which became bound to the plastic in the presence of a monoclonal antibody which does not bind hCG) was subtracted.
*p < .001; all the others are not significantly different from zero.

TABLE III

Statistical Analysis of the Affinity of B101 F(ab')$_2$
Compared with the Affinity of B101 F(ab')$_2$ + B102

| Experiment | Antibody or Mixture | Keq*(L/nMole) | Enhancement Factor** | P |
|---|---|---|---|---|
| 1 | B101 F(ab')$_2$ | 1.61 ± 0.18*** | 1.5 | <.1 |
| | B101 F(ab')$_2$ + B102 | 2.4 ± 0.4 | | |
| 2 | B101 F(ab')$_2$ | 0.77 ± 0.11 | 2.2 | <.01 |
| | B101 F(ab')$_2$ + B102 | 1.7 ± 0.1 | | |
| 3 | B101 F(ab')$_2$ | 0.97 ± 0.17 | 2.0 | <.01 |
| | B101 F(ab')$_2$ + B102 | 1.9 ± 0.2 | | |
| 4 | B101 F(ab')$_2$ | 0.72 ± 0.06 | 6.4 | <.01 |
| | B101 F(ab')$_2$ + B102 | 4.6 ± 0.8 | | |

*Determined using Scatchard plots [Scatchard, G., (1949) Ann. N.Y. Acad. Sci. 52:660.]
**Keq for a mixture of B101 F(ab')$_2$ and B102 divided by Keq for B101.
***Keq values for B101 F(ab')$_2$ are not significantly different than Keq for B101 shown in Table I.

Discussion

Mixtures of monoclonal antibodies may have significantly different properties than the individual components. It has been shown that the affinity of a mixture of hybridoma antibodies can be enhanced. Other properties of monoclonal antibodies have previously been improved by utilizing more than one hybridoma antibody. Haber, et al. [Haber, E. et al., (1980) "Resolving antigenic sites and purifying proteins with monoclonal antibodies", Monoclonal Antibodies in Endocrine Research, Raven Press] developed a radioimmunometric assay with two monoclonal antibodies which had greater specificity than an assay employing either antibody separately. Howard, et al. [Howard, J. C., et al., (1979) Immunological Rev. 47: 139] showed that combinations of monoclonal antibodies can be synergistic in lysing red blood cells. Although some of the advantages of monoclonal antibodies may be lost upon mixing, such as the ability to react with a single determinant, many advantages may result in producing what is, in effect, a synthetic antiserum. These results may also have implications for the control of antibody synthesis and the immune response in vivo. Since mixtures of antibodies have different properties than the individual antibodies (depending on which ones are mixed), it seems likely that the immune response should result in mixtures of compatible antibodies. Thus, the maturation of the affinity of antisera [Karush, E., (1978) Comprehensive Immunology 5. Immunoglobulins pp. 85, Plenum Medical Book Co., New York] may not only be due to the fact that a high affinity clone has been stimulated but that an antibody has been produced which can enhance the affinity of another antibody already present in the serum.

Several types of antibody mixtures have been examined. Combining antibody B101 with antibody A102 results in the expected dose-response curve in that the logic plot shows the inhibition line for the mixture to be between the inhibition curves for the separate antibodies. B101 and A102 cannot bind hCG simultaneously. With antibodies B101 and B103, which can bind to the hormone at the same time, the logit plot for the mixture follows the plot for the high affinity antibody at low antigen concentrations and approaches the line for the low affinity antibody at high antigen concentrations. The mixture of antibodies B101 and B102 is the major result of this work in that the affinity of the mixture is higher than either antibody. As shown in Table I, this result is reproducible and statistically significant.

Once the presence of a cooperative effect had been established, the question of mechanism arose. There was a loss of enhancement when the F(ab) fragment was substituted for the antibody. This result indicates two important characteristics of the cooperativity. First, a larger fragment of the antibody than F(ab) is required. Second, the possibility that the binding of one antibody changes the conformation of the hormone thus leading to a higher affinity of the second antibody (an allosteric model) became unlikely. Another possible explanation for the enhancement is that it is caused by intermolecular crosslinking of bivalent antibodies and antigen (as in formation of a circular complex consisting of two antibody and two antigen molecules, which Schumaker, et al. [Schumaker, V. N., et al., (1973) Immunochemistry 10: 521] have predicted to be very stable complexes). The results with F(ab')$_2$ indicate that, at the very least, this cannot be the sole mechanism. Alternatively, interaction of the F(c) regions in a complex is consistent with all data from the liquid phase radioimmunoassays. The solid phase assays seem to indicate the F(c) interactions are not the only factor since the antibodies are already anchored to the plastic and enhancement still occurs. Of course, the mechanism may be different for the two types of assays. Finally, the results with antibodies B101 and B103, which can bind simultaneously to hCG but do not have a cooperative interaction, indicate that idiotype-anti-idiotype interactions may play a role (i.e., B101 and B102 may have an idiotype-anti-idiotype interaction between the free F(ab) arms left after binding to hCG while B101 and B103 are not related in this way). It should be emphasized, however, that the fact that B101 and B103 are not enhancing argues very strongly that some characteristic of the individual antibody (such as spatial orientation of the epitope or the nature of the idiotope) is extremely important in the cooperative effect. Further experiments are necessary for complete characterization of the mechanism.

The possibility that mixtures of antibodies may have higher affinity than the individual antibodies has two major implications. First, an opportunity for increasing the affinity of monoclonal antibodies is provided. Second, the capacity to mix a series of antibodies in a defined system makes possible a more complete understanding of the subtle effects which occur in a polyclonal immune sera.

Extent of Synergistic Interactions

By performing radioimmunoassays with all paired combinations of five monoclonal antibodies, the prevalence of synergistic interactions was measured. The following table shows the pairs of antibodies that are synergistic (have a higher affinity for antigen when mixed) measured by double antibody radioimmunoassays. A plus sign indicates that the antibody identified at the top of the column is synergistic with the antibody named at the left. A minus sign indicates no synergistic interaction.

| Antibody | A103 | B101 | B102 | B103 |
|---|---|---|---|---|
| A102 | − | − | + | + |
| A103 |   | − | + | + |
| B101 |   |   | + | − |
| B102 |   |   |   | − |

Thus, out of ten possible pairs, five are synergistic. Actually, the proportion is much higher because some of these antibodies cannot bind antigen simultaneously under any conditions. If these pairs are eliminated, then 5 out of 7 pairs are synergistic.

Increase in Specificity of Mixtures of Monoclonal Antibodies

FIG. 7 shows the logit inhibition curves of a mixture of B101 and B102, antibody B101, and antibody B102 with hCG (the antigen) and hLH (a hormone with a very similar structure). Distinguishing between these two hormones is very important in the diagnosis of pregnancy and cancer. Graph A shows that the mixture of B101 and B102 can bind hCG about 170 fold stronger than hLH. Graph B shows that B101 can bind hCG about 50 fold stronger than hLH. Graph C shows that B102 is more sensitive to hCG than hLH by about 10 fold. Therefore, the mixture of antibodies is more specific than the individual antibodies.

In order to further characterize those monoclonal antibodies which when mixed provide enhanced affinity for antigen, further studies were undertaken. These studies showed that monoclonal antibodies possessing this property could be differentiated from those which do not, based upon ability to form a stable complex between the mixture of antibodies and the antigen. This complex appeared as an extra band in gel electrophoresis.

More specifically, 1–5 μg hCG and 1–5 μg antibody mixture were placed in 11 cm long tubes of 3, 4, 5, 6 and 7 percent polyacrylamide gels. The tubes were then subjected to a constant current of 4 milliamps per tube. The method used is essentially the same as that described for the second dimension in O'Farrell, P. H. (1975) J. Biol. Chem. 250: 4007–4021, except that there is no SDS. After separation, the gels are stained with a suitable dye.

The appearance of an extra band based upon the formation of a complex between the monoclonal antibody mixture and antigen indicates that use of such monoclonal antibody mixtures in assays for the appropriate antigen will provide enhanced sensitivity.

In addition to electrophoresis, antibody combinations resulting in enhanced affinity were recognized by an extra high molecular weight peak on gel filtration chromatography. More specifically, 1–5 μg hCG containing a suitable amount of radioiodinated hCG (0.1–10.0 Ci) were mixed with 1 to 10 micrograms of the antibody mixture and chromatographed in 0.015M Hepes buffer, pH 7.4–0.9% NaCl—1 μg/ml BSA over a 1 cm diameter—24 cm long Sephacryl S-400 column. Mixtures of B101+B102+hCG giving enhanced affinity gave rise to an extra peak whereas mixtures of B101+B103+hCG known not to give an increase in affinity in solution failed to produce the extra peak. Thus, this procedure is also useful in determining which pairs of antibody will be effective.

Although the invention has been described with particular reference to the use of mixtures of monoclonal antibodies in assays to provide enhanced sensitivity, it is understood that the invention also embraces use of the mixtures to provide enhanced specificity and such other purposes as may subsequently be discovered, including perhaps in vivo treatment methods for various conditions.

What is claimed is:

1. A method for obtaining at least two monoclonal antibodies specific for an antigen, each of which binds to a different antigenic site on the antigen, the monoclonal antibodies being characterized by imparting enhanced sensitivity when incorporated into immunoassays for the antigen comprising:
   a. preparing and separately recovering a plurality of monoclonal antibodies which bind to the antigen;
   b. screening the monoclonal antibodies so recovered by gel electrophoresis to identify monoclonal antibodies which bind to different antigenic sites on the antigen and which are capable of forming a stable complex which includes the antigen and the monoclonal antibodies by preparing mixtures containing at least two of the monoclonal antibodies recovered in step (a), treating each such mixture in the presence of the antigen so as to form stable complexes between the antigen and those monoclonal antibodies which bind to different antigenic sites on the antigen, detecting the complexes so formed and thereby identifying the monoclonal antibodies; and
   c. recovering the monoclonal antibodies so identified and thereby obtaining antibodies which impart enhanced sensitivity when incorporated into immunoassays for the antigen.

2. A method for obtaining at least two monoclonal antibodies specific for an antigen, each of which binds to a different antigenic site on the antigen, the monoclonal antibodies being characterized by imparting enhanced sensitivity when incorporated into immunoassays for the antigen comprising:
   a. preparing and separately recovering a plurality of monoclonal antibodies which bind to the antigen;
   b. screening the monoclonal antibodies so recovered by gel filtration chromatography to identify monoclonal antibodies which bind to different antigenic sites on the antigen and which are capable of forming a stable complex which includes the antigen and the monoclonal antibodies by preparing mixtures containing at least two of the monoclonal antibodies recovered in step (a), treating each such mixture in the presence of the antigen so as to form stable complexes between the antigen and those monoclonal antibodies which bind to different antigenic sites on the antigen, detecting the complexes so formed and thereby identifying the monoclonal antibodies; and
   c. recovering the monoclonal antibodies so identified and thereby obtaining antibodies which impart enhanced sensitivity when incorporated into immunoassays for the antigen.

* * * * *